(12) United States Patent
Yamamoto

(10) Patent No.: US 7,887,656 B2
(45) Date of Patent: Feb. 15, 2011

(54) MANUFACTURING METHOD OF ABSORBENT ARTICLE

(75) Inventor: Hiroki Yamamoto, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 175 days.

(21) Appl. No.: 12/389,974

(22) Filed: Feb. 20, 2009

(65) Prior Publication Data

US 2010/0116409 A1     May 13, 2010

(30) Foreign Application Priority Data

Nov. 11, 2008   (JP) .............................. 2008-289309

(51) Int. Cl.
  *B32B 37/00*   (2006.01)
(52) U.S. Cl. .................. 156/73.1; 156/64; 156/269
(58) Field of Classification Search .................. 156/64, 156/73.1, 250, 267, 269, 580.1, 580.2; 228/1.1, 228/110.1; 264/442, 443, 444, 445
See application file for complete search history.

(56) References Cited

U.S. PATENT DOCUMENTS 7,122,097 B2 * 10/2006 Rabe ........................ 156/580.2
7,150,388 B2 * 12/2006 Matsumura ............... 228/110.1
7,371,297 B2 * 5/2008 Caroli ......................... 156/64

FOREIGN PATENT DOCUMENTS

JP         05-015551 A         1/1993

\* cited by examiner

*Primary Examiner*—James Sells
(74) *Attorney, Agent, or Firm*—Lowe, Hauptman, Ham & Berner, LLP

(57) ABSTRACT

In the present invention, ultrasonic vibration is outputted to predetermined regions of a first web and a second web from an output surface of an ultrasonic horn so that the predetermined regions may be bonded. The output surface includes a central output portion in a center region of three equal regions into which each predetermined region is divided, and both-ends output portions in both-ends regions at sides of the center region. A central maximum amplitude of the ultrasonic vibration outputted from the central output portion is smaller than an end maximum amplitude of the ultrasonic vibration outputted from each of the both-ends output portions. A central bonding strength of the center region is smaller than an end bonding strength of each of the both-ends regions.

7 Claims, 11 Drawing Sheets

FIG. 1
(a)
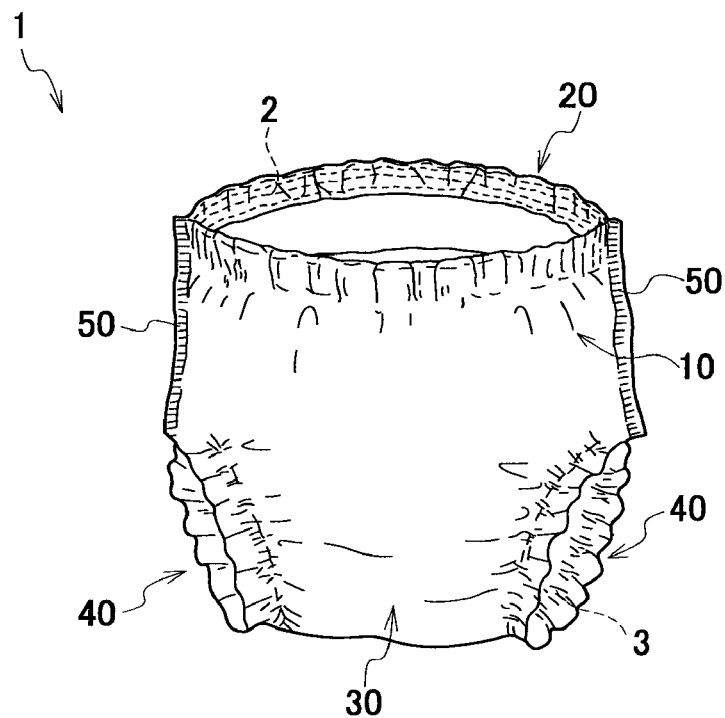
(b)
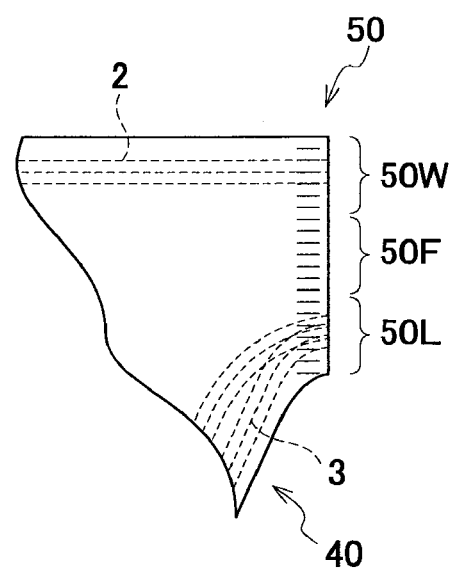

FIG. 8
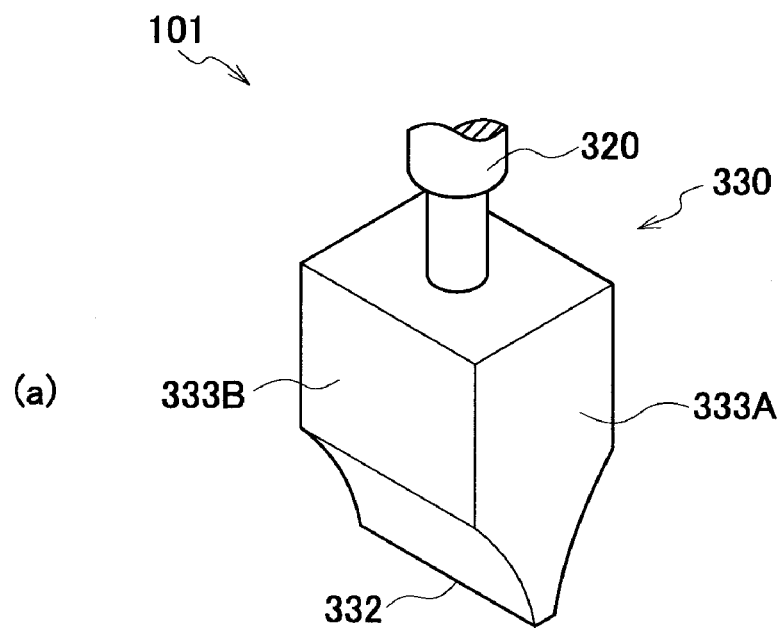
(a)
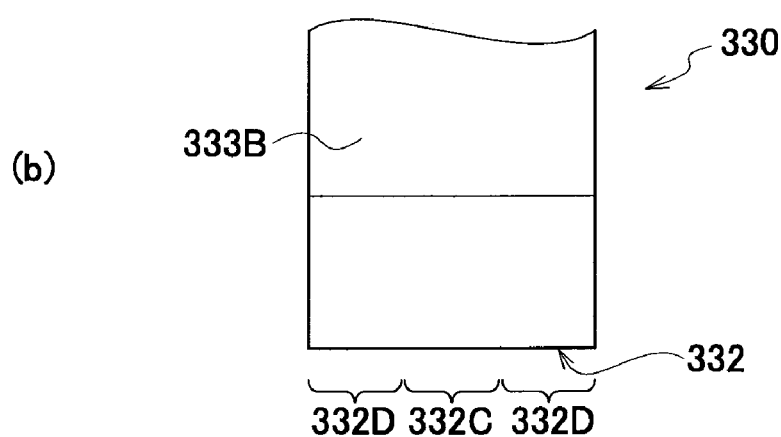
(b)

FIG. 9
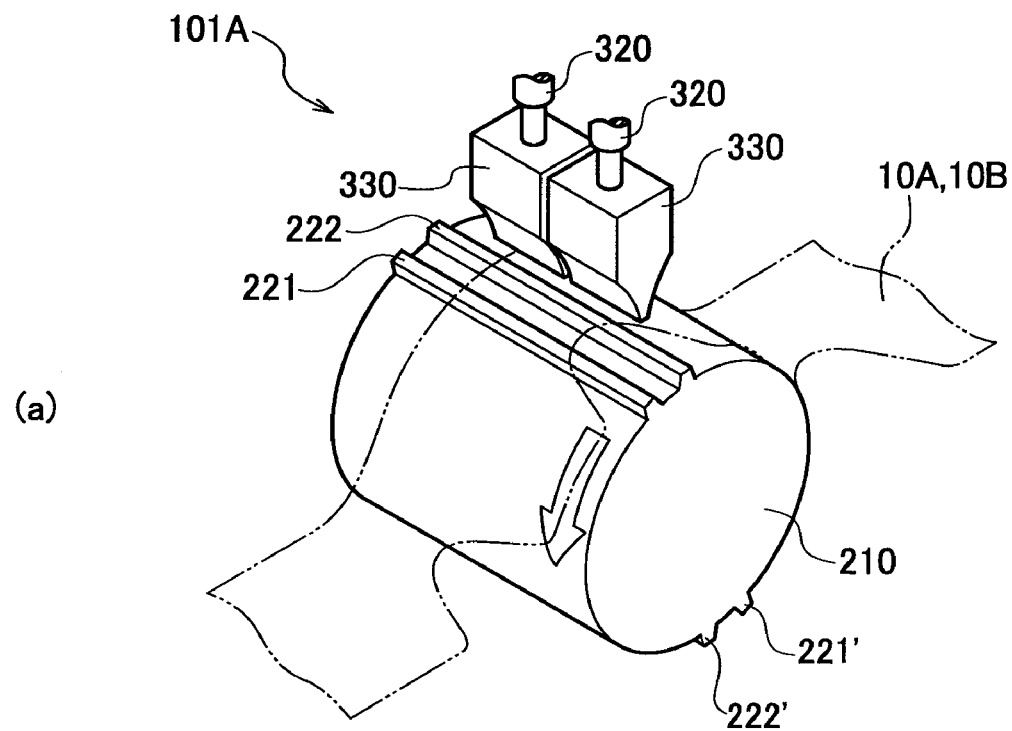
(a)
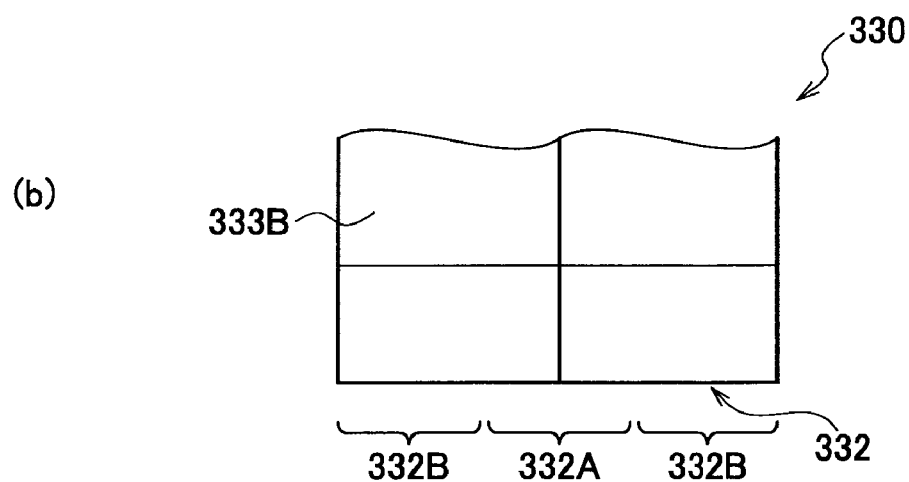
(b)

FIG. 10
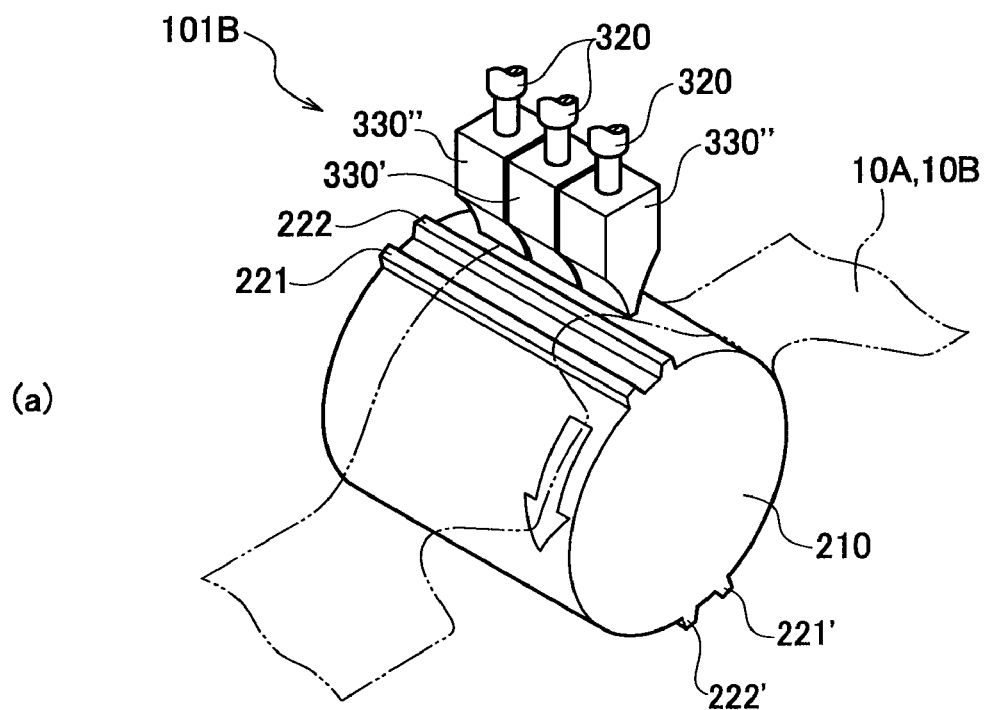
(a)
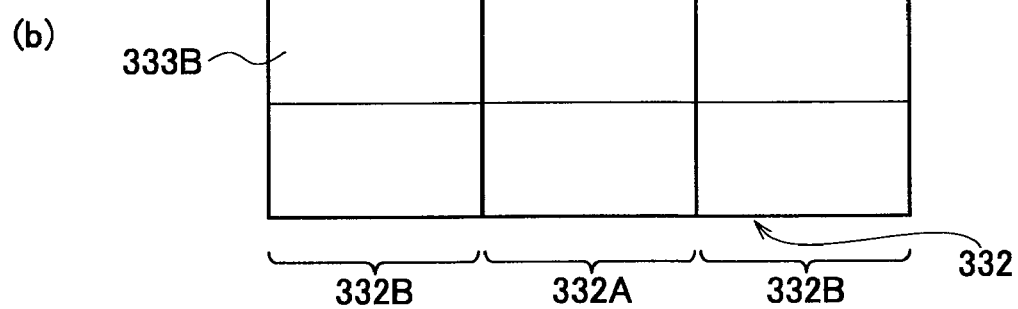
(b)

MANUFACTURING METHOD OF ABSORBENT ARTICLE

RELATED APPLICATIONS

The present application is based on, and claims priority from, Japanese Application Number 2008-289309, filed Nov. 11, 2008, the disclosure of which is hereby incorporated by reference herein in its entirety.

BACKGROUND OF THE INVENTION

1. Field of the Invention

The present invention relates to a manufacturing method of an absorbent article including a first web which constitutes a front waistband part, and a second web which constitutes a rear waistband part.

2. Description of the Related Art

Generally, an absorbent article, such as a disposable diaper, includes: a front waistband part which corresponds to a front portion around the waistline of a wearer; a rear waistband part which corresponds to a rear portion around the waistline of the wearer; a crotch part which corresponds to the crotch of the wearer; and leg openings which open at sides of the crotch part.

The front waistband part and the rear waistband part are bonded to each other from an upper edge portion of the absorbent article from which a waistline portion of the wearer is to be inserted (i.e., an edge portion corresponding to a waist portion of the wearer) to each leg opening. These portions where the front and rear waistband parts are bonded to each other (hereinafter, referred to as bonded part) are each formed of a waist portion including a waist gather, a leg portion including a leg gather, and a fit portion located between the waist gather and the leg gather.

A manufacturing method of such an absorbent article includes a step of bonding predetermined regions of the first web which constitutes the front waistband part and the second web which constitutes the rear waistband part which are in a overlapped state, the predetermined regions provided to the first web and the second web with a predetermined interval in a conveyance direction of the first web and the second web, and each corresponding to a bonded part.

For example, there is known a technique of bonding a first web and a second web by outputting ultrasonic vibration to a predetermined region using an ultrasonic bonding device (for example, see Japanese Patent Application Publication No. Hei 5-15551 (pages 2 and 3, and FIG. 4)). The ultrasonic bonding device includes an anvil roll which supports the first web and the second web, and an ultrasonic mechanism which faces the anvil roll and which outputs the ultrasonic vibration to the predetermined region between itself and the anvil roll.

Specifically, the ultrasonic mechanism includes an ultrasonic vibrator (oscillator) which generates ultrasonic vibration, and an ultrasonic horn (vibrator) which outputs the ultrasonic vibration generated by the ultrasonic vibrator to the predetermined region. The ultrasonic horn includes an input surface for receiving the ultrasonic vibration generated by the ultrasonic vibrator, and an output surface for outputting the ultrasonic vibration inputted to the input surface to the predetermined region. Note that, in order to output the ultrasonic vibration to the predetermined region as equally as possible, the ultrasonic vibrator and the vibrator are connected in an input center region corresponding to an output center region, the input center region including the center of the input surface, the output center region including the center of the output surface.

However, the aforementioned conventional technique has the following problems. Specifically, since the ultrasonic vibrator is connected to the ultrasonic horn in the input center region, the ultrasonic vibration having inputted to the input surface from the ultrasonic vibrator is outputted in a manner of decreasing from the output center region corresponding to the input center region with distance from the output center region. In other words, the output of the ultrasonic vibration decreases with distance from the output center region.

This makes the bonding strength of the first web and the second web in a region corresponding to each fit portion stronger than the bonding strength of the first web and the second web in a region corresponding to each waist portion, as well as than the bonding strength of the first web and the second web in a region corresponding to each leg portion.

Therefore, when a wearer puts on and off an absorbent article (at the time of putting on and off), the waist portion and the leg portions can be separated easily, which consequently reduces the durability of the absorbent article. Further, if the waist portion can be separated easily, the absorbent article is less likely to fit the waist portion of the wearer while the wearer wears the absorbent article (while being worn). Meanwhile, if the leg portions can be separated easily, the absorbent article is less likely to fit around the legs of the wearer while being worn. Accordingly, excrement from the wearer may leak from the absorbent article (a so-called leakage prevention capability may be deteriorated).

Conceivable methods for addressing the above problems include strongly bonding the whole predetermined region (that is, increasing the entire bonding strength). However, if the bonding strength of the whole predetermined region is increased, it becomes difficult to tear the bonded part (a so-called disassembling property is deteriorated) when the wearer disposes the absorbent article (at the time of disposal).

As described above, in addition to basic properties originally needed, such as the improvement of the durability of the absorbent article at the time of putting on and off and the leakage prevention capability while being worn, it is required for the absorbent article to have additional properties contradictory to the basic properties, such as the disassembling property required when the wearer disposes the absorbent article (at the time of disposal).

SUMMARY OF THE INVENTION

Thus, an object of the present invention is to provide a manufacturing method of an absorbent article capable of making a waist portion and a leg portion of the absorbent article less likely to be separated while keeping the basic properties, such as the durability and the leakage prevention capability of the absorbent article, and the additional properties, such as the disassembling property thereof, when a predetermined region corresponding to a bonded part of the absorbent article is bonded by using an ultrasonic bonding device.

In order to solve the problem described above, the present invention has the following feature. A first feature of the present invention is a manufacturing method of an absorbent article including a first web (first web 10A) which constitutes a front waistband part (front waistband part 10), and a second web (second web 20A) which constitutes a rear waistband part (rear waistband part 20). The method includes: a step A of conveying the first web and the second web in an overlapped state between an anvil part (projecting part 220) and a vibrator (ultrasonic horn 330) which are provided to an ultrasonic bonding device (for example, ultrasonic bonding device 100); and a step B of bonding predetermined regions (predetermined region 60) provided to the first web and the second web with a predetermined interval in a conveyance direction of the first web and the second web by outputting the ultrasonic vibration from an output part (output surface 332) of the vibrator to the predetermined regions, the ultrasonic vibration generated by an oscillator (ultrasonic vibrator 310) provided to the ultrasonic bonding device. In the method, the output part includes: a central output portion (central output portion 332A) configured to output the ultrasonic vibration to a center region (center region 60C) of three equal regions into which each predetermined region is divided in a cross direction crossing the conveyance direction; and both-ends output portions (both-ends output portions 332B) configured to output the ultrasonic vibration respectively to both-ends regions (both-ends regions 60S) of the three equal regions into which each predetermined region is divided, the both-ends regions located at both sides in the cross direction of the center region, a central maximum amplitude of the ultrasonic vibration outputted from the central output portion to the center region is smaller than an end maximum amplitude of the ultrasonic vibration outputted from each of the both-ends output portions to a corresponding one of the both-ends regions, and a central bonding strength of the center region bonded by the central output portion is smaller than an end bonding strength of each of the both-ends regions bonded by a corresponding one of the both-ends output portions.

According to the present invention, it is possible to provide a manufacturing method of an absorbent article capable of making a waist portion and a leg portion of the absorbent article less likely to be separated while keeping basic properties, such as the durability and the leakage prevention capability of the absorbent article, and additional properties, such as the disassembling property thereof, when a predetermined region corresponding to a bonded part of the absorbent article is bonded by using an ultrasonic bonding device.

BRIEF DESCRIPTION OF THE DRAWINGS

FIG. 1 is a view showing an absorbent article 1 according to this embodiment.

FIG. 8 is a view showing an ultrasonic bonding device 101 according to a modification.

FIG. 9 is a view showing an ultrasonic bonding device 101A according to a first modification.

FIG. 10 is a view showing an ultrasonic bonding device 101B according to a second modification (No. 1).

DESCRIPTION OF THE PREFERRED EMBODIMENT

Figure 2:
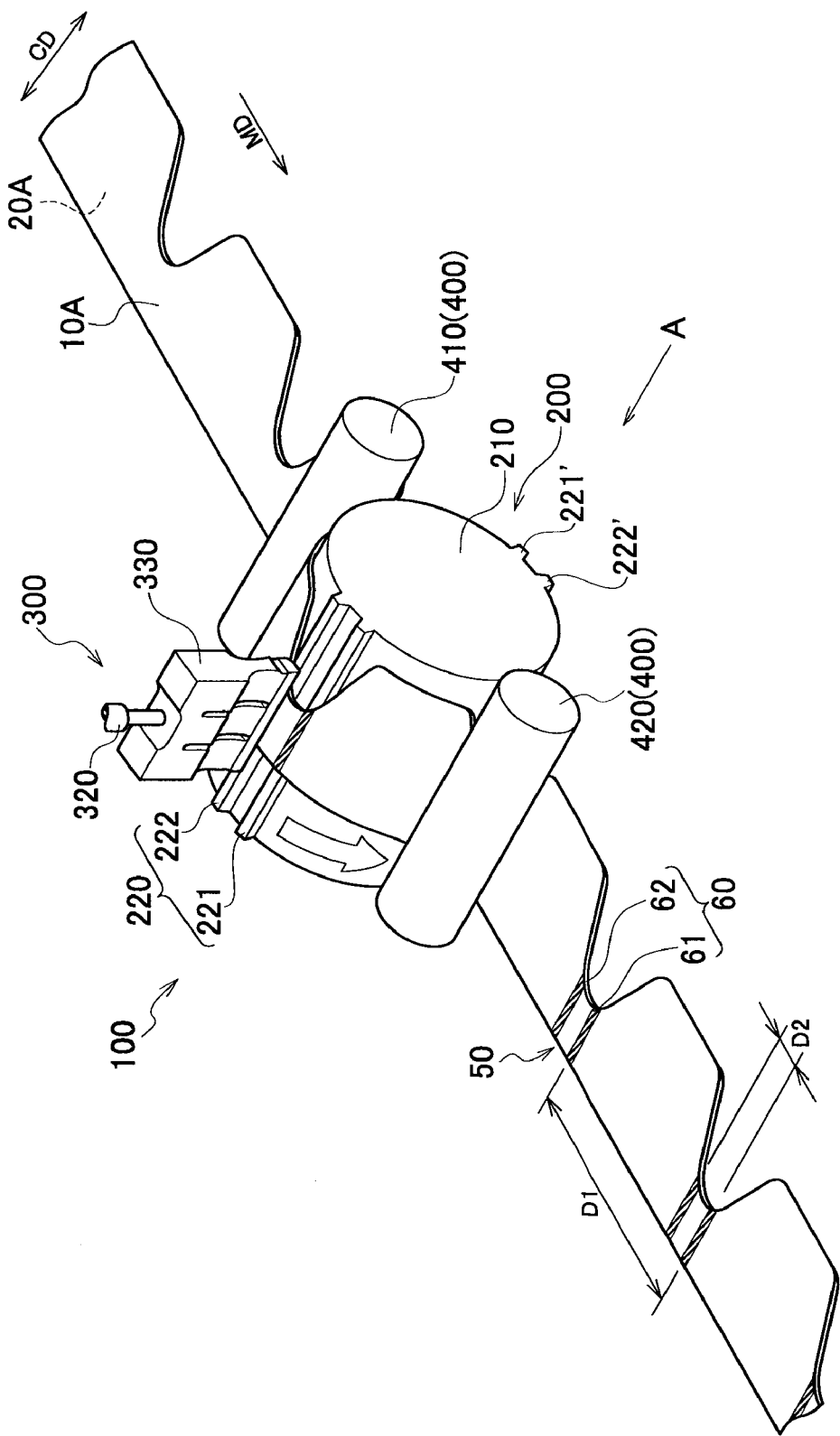
FIG. 2 is a perspective view showing an ultrasonic bonding device 100 according to this embodiment.

Hereinafter, a manufacturing method of an absorbent article according to the present invention will be described with reference to the drawings. Specifically, (1) structure of absorbent article, (2) configuration of ultrasonic bonding device, (3) working of ultrasonic bonding device, (4) manufacturing method of absorbent article, (5) operation and effect, (6) modifications, and (7) other embodiments will be described.

Note that, in the description of the following drawings, the same or similar reference numerals are given to the same or similar parts. However, it should be noted that the drawings are schematic and proportions of respective dimensions and the like differ from actual ones.

Therefore, a concrete size and the like should be determined in consideration of the following description. Further, it is needless to say that the drawings contain parts where relations and proportions of the dimensions are different from one another.

(1) Structure of Absorbent Article

First, a structure of an absorbent article 1 according to this embodiment will be described with reference to the drawings. FIG. 1(*a*) is a perspective view showing the absorbent article 1 according to this embodiment. FIG. 1(*b*) is a plan view (front view) showing the absorbent article 1 according to this embodiment.

As shown in FIG. 1, the absorbent article 1 is provided with a front waistband part 10 corresponding to a front portion around the hip of a wearer, a rear waistband part 20 corresponding to a rear portion around the hip of the wearer, a crotch part 30 corresponding to the crotch of the wearer, leg openings 40 which open in side portions of the crotch part 30.

The front waistband part 10 and the rear waistband part 20 are bonded to each other from an upper edge portion of the absorbent article 1 into which a hip portion of the wearer is to be inserted (i.e., an edge portion corresponding to a waist portion of the wearer), to the leg openings 40. This portion bonded to each other (hereinafter, bonded part 50) is formed of a waist portion 50W including a waist gather 2, a leg portion 50L including a leg gather 3, and a fit portion 50F located between the waist gather 2 and the leg gather 3.

Figure 3:
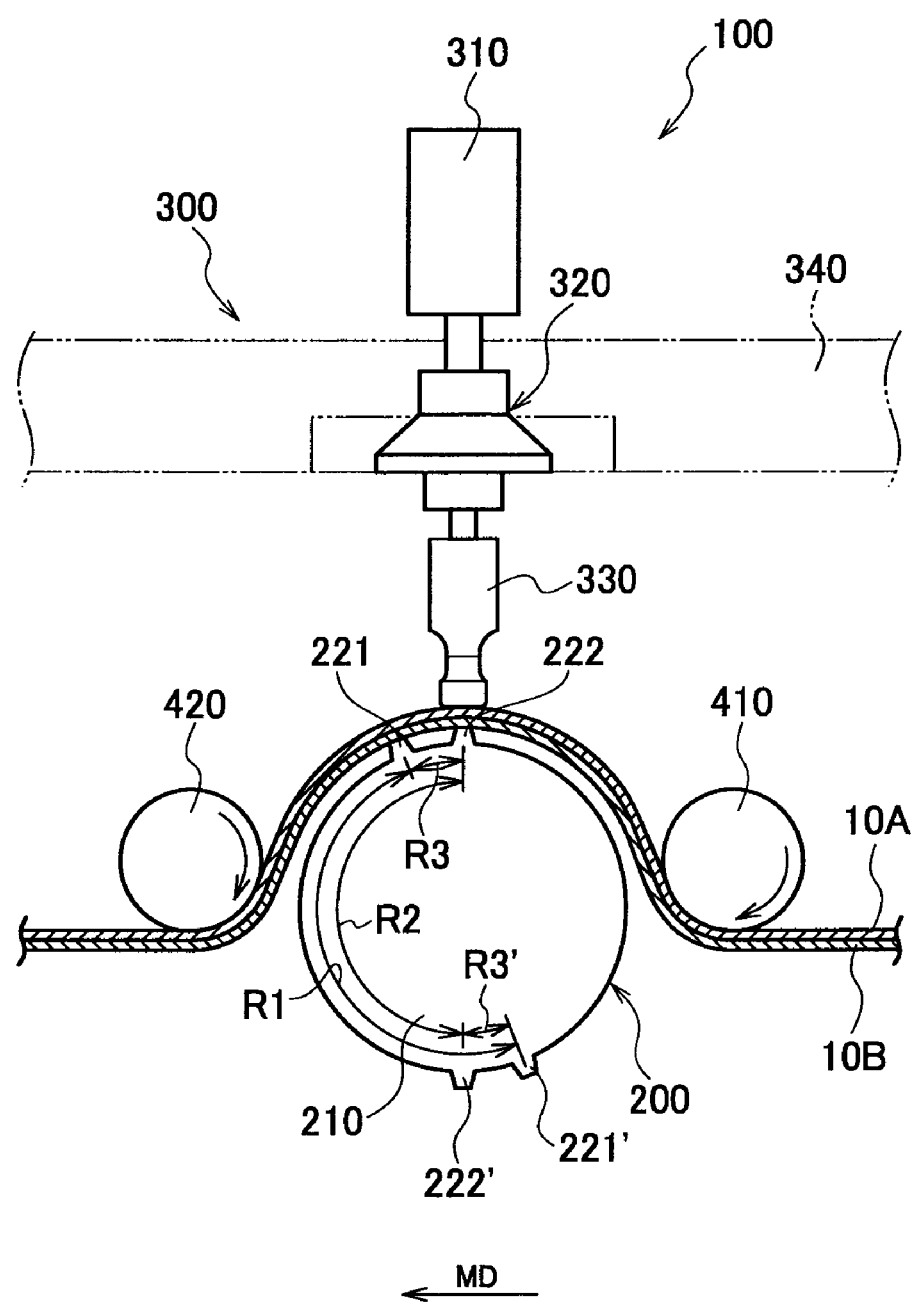
FIG. 3 is a side view (view along an arrow A of FIG. 2) showing the ultrasonic bonding device 100 according to this embodiment.

The front waistband part 10 and the rear waistband part 20 is stretchy in a conveyance direction MD of a first web 10A which constitutes the front waistband part 10 (see FIG. 2 or 3), and a second web 20A which constitutes the rear waistband part 20 (see FIG. 2 or 3). For example, the front waistband part 10 and the rear waistband part 20 may be stretchy in the conveyance direction MD by being provided with the above-described waist gather 2, and may be stretchy in the conveyance direction MD by forming the first web 10A and the second web 20A themselves with a stretchy sheet.

The crotch part 30 is stretchy in a cross direction CD crossing the conveyance direction MD. For example, the crotch part 30 may be stretchy in the cross direction CD by being provided with the above-described leg gather 3, and may be stretchy in the cross direction CD by forming the first web 10A and the second web 20A themselves with a stretchy sheet.

(2) Configuration of Ultrasonic Bonding Device

Next, a configuration of an ultrasonic bonding device 100 according to this embodiment will be described with reference to the drawings. FIG. 2 is a perspective view showing the ultrasonic bonding device 100 according to this embodiment. FIG. 3 is a side view (view along an arrow A of FIG. 2) showing the ultrasonic bonding device 100 according to this embodiment.

As shown in FIGS. 2 and 3, the ultrasonic bonding device 100 bonds the first web 10A and the second web 20A by outputting ultrasonic vibration to a predetermined region 60. The ultrasonic bonding device 100 includes an anvil roll 200, an ultrasonic mechanism 300, and guide rolls 400.

(2-1) Configuration of Anvil Roll

First, a configuration of the anvil roll 200 will be described with reference to FIGS. 2 and 3. As shown in FIGS. 2 and 3, the anvil roll 200 conveys the first web 10A and the second web 20A in the conveyance direction MD while supporting the first web 10A and the second web 20A.

The anvil roll 200 is formed in a cylindrical shape, and is provided with a body part 210 which rotates in the conveyance direction MD centering on a center shaft (not shown), and projecting parts 220 (anvil parts) which are provided in an outer circumference of the anvil roll 200 and project outward in a diameter direction of the anvil roll 200 from the body part 210.

The projecting parts 220 come into contact with an ultrasonic horn 330 which constitutes the ultrasonic mechanism 300 to be described later with the first web 10A and the second web 20A interposed therebetween. In other words, the projecting parts 220 work with the ultrasonic mechanism 300 to pinch the first web 10A and the second web 20A.

The multiple projecting parts 220 are provided independently. The independent projecting parts 220 are arranged so as to be aligned in the conveyance direction MD in the body part 210. Specifically, the projecting part 220 includes two first projecting parts 221, 221' respectively provided in positions shifted by half of the diameter of the anvil roll 200 and two second projecting parts 222, 222' which are adjacent to the rear side in a rotational direction of the first projecting parts 221, 221', respectively.

The first projecting parts 221, 221' and the second projecting parts 222, 222' are arranged to fit into the predetermined regions 60 of the first web 10A and the second web 20A, the predetermined regions 60 arranged with a predetermined interval (D1) in the conveyance direction MD.

Here, the predetermined region 60 corresponds to the bonded part 50 of the absorbent article 1. Specifically, the predetermined region 60 is formed of a first predetermined region 61, and a second predetermined region 62 which is adjacent to the first predetermined region 61 at an interval (D2) smaller than the predetermined interval (D1) in the conveyance direction MD.

In other words, as shown in FIG. 3, a rotation distance (R1) between the first projecting parts 221, 221' and a rotation distance (R2) between the second projecting parts 222, 222' correspond to a distance between the first predetermined regions 61 (i.e., the above-described predetermined interval (D1)). Further, a rotation distance (R3) from the first projecting part 221 to the second projecting part 222 and a rotation distance (R3') from the first projecting part 221' to the second projecting part 222' correspond to a distance from the first predetermined region 61 to the second predetermined region 62 (i.e., the above-described interval (D2)).

Here, although the projecting parts 220 include a total of four projecting parts of the two first projecting parts 221, 221' and the two second projecting parts 222, 222', the number of the projecting parts 220 is not necessary to be four and the arrangement interval and the number thereof are selected suitably in accordance with the diameter of the anvil roll 200.

(2-2) Configuration of Ultrasonic Mechanism

Figure 4:
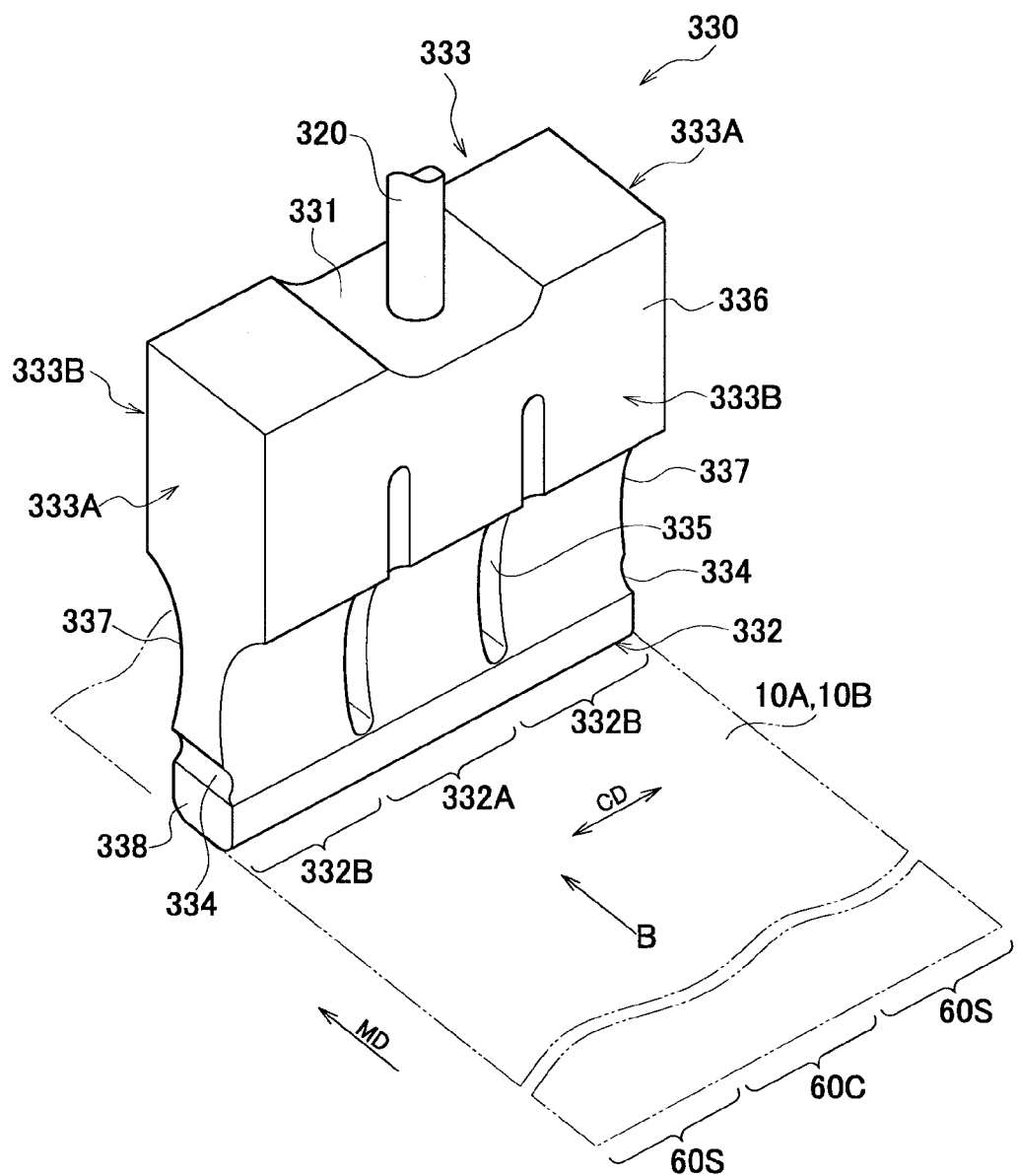
FIG. 4 is a perspective view showing an ultrasonic mechanism 300 according to this embodiment.
Figure 5:
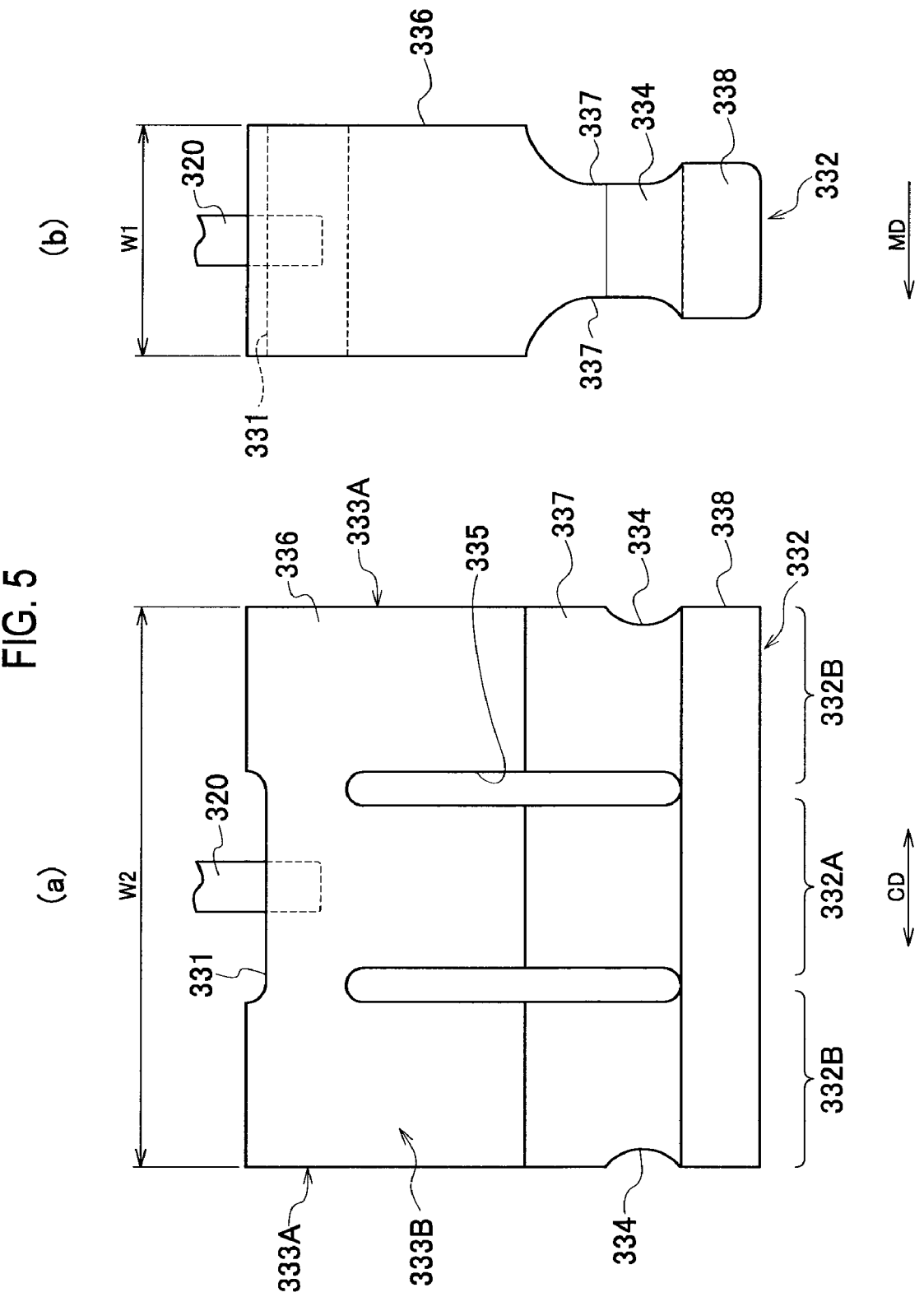
FIG. 5 is a plan view showing the ultrasonic mechanism 300 according to this embodiment.

Next, a configuration of the ultrasonic mechanism 300 will be described with reference to FIGS. 2 to 5. FIG. 4 is a perspective view showing the ultrasonic mechanism 300 according to this embodiment. FIG. 5(a) is a front view (view along an arrow B of FIG. 4) showing the ultrasonic mechanism 300 according to this embodiment. FIG. 5(b) is a side view (view along an arrow C of FIG. 4) showing the ultrasonic mechanism 300 according to this embodiment.

As shown in FIGS. 2 and 3, the ultrasonic mechanism 300 works with the first projecting parts 221, 221' and the second projecting parts 222, 222' to pinch the first web 10A and the second web 20A, so that the ultrasonic vibration is applied to the predetermined region 60 of the first web 10A and the second web 20A. The ultrasonic mechanism 300 is provided with an ultrasonic vibrator 310 (oscillator), a booster 320, and the ultrasonic horn 330 (vibrator).

(2-2-1) Ultrasonic Vibrator

As shown in FIG. 3, the ultrasonic vibrator 310 emits ultrasonic vibration to the ultrasonic horn 330 via the booster 320. The ultrasonic vibrator 310 is connected to the booster 320.

(2-2-2) Booster

As shown in FIG. 3, the booster 320 amplifies the ultrasonic vibration outputted from the ultrasonic vibrator 310. The booster 320 is fixed to a pressing arm 340 which adjusts a height of the ultrasonic horn 330. The booster 320 transmits the amplified ultrasonic vibration to the ultrasonic horn 330.

(2-2-3) Ultrasonic Horn

As shown in FIG. 3, the ultrasonic horn 330 presses the predetermined region 60 corresponding to the bonded part 50 of the absorbent article 1 toward a side of the anvil roll 200, and applies the ultrasonic vibration to the predetermined region 60. In other words, the ultrasonic horn 330 works with the first projecting parts 221, 221' and the second projecting parts 222, 222' to pinch the predetermined region 60. The ultrasonic horn 330 is connected to the pressing arm 340 via the booster 320.

As shown in FIGS. 4 and 5, the ultrasonic horn 330 has a width (W2) in the cross direction CD larger than a width (W1) in the conveyance direction MD. The ultrasonic horn 330 includes an input surface 331 to which the ultrasonic vibration generated by the ultrasonic vibrator 310 is inputted, an output surface 332 (output part) which outputs the ultrasonic vibration inputted to the input surface 331 to the predetermined region 60, and a side surface 333 provided between the input surface 331 and the output surface 332.

The booster 320 is connected to an input center region including the center of the input surface 331. The input center region of the input surface 331 is dented more than regions at the outside of the input center region in the cross direction CD.

The output surface 332 includes a central output portion 332A which outputs the ultrasonic vibration to a center region 60C of three equal regions into which the predetermined region 60 is divided with respect to the cross direction CD, and both-ends output portions 332B which output the ultrasonic vibration to both-ends regions 60S, located at both sides in the cross direction CD of the center region 60C, of the three equal regions into which the predetermined region 60 is divided.

The side surface 333 is a surface along the conveyance direction MD, and includes a pair of first side surfaces 333A facing each other, and a pair of second side surfaces 333B having surfaces along the cross direction CD whose widths are wider than those of the first side surfaces 333A, and facing each other.

In each first side surface 333A, a notch portion 334 is formed which is concaved in an arc shape from one first side surface 333A toward the other first side surface 333A. In the second side surfaces 333B, through-hole portions 335 are formed which penetrate from one second side surface 333B toward the other second side surface 333B.

The ultrasonic horn 330 includes a large width portion 336 having a large width between the second side surfaces 333B (i.e., a distance in the conveyance direction MD), a small width portion 337 having a distance between the second side surfaces 333B smaller than that of the large width portion 336, and a middle width portion 338 having a distance between the second side surfaces 333B smaller than that of the large width portion 336 and a width in the conveyance direction MD larger than that of the small width portion 337, in the view seen from a side (FIG. 5(b)) of the ultrasonic horn 330.

The large width portion 336 is located on a side closer to the input surface 331 than the center in a height direction of the ultrasonic horn 330. The small width portion 337 is located on a side closer to the output surface 332 than the large width portion 336. The large width portion 336 continues into the small width portion 337 in an arc shape. The middle width portion 338 is located closer to the side of the output surface 332 than the small width portion 337. The small width portion 337 continues into the middle width portion 338 in an arc shape.

(2-3) Configuration of Guide Roll

The guide rolls 400 support the first web 10A and the second web 20A. Specifically, the guide roll 400 includes a first guide roll 410, and a second guide roll 420 which is provided at a rear side in the conveyance direction MD than the first guide roll 410.

The first guide roll 410 leads the first web 10A and the second web 20A between the anvil roll 200 and the ultrasonic horn 330. The second guide roll 420 guides the first web 10A and the second web 20A to a next step after the first web 10A and the second web 20A have passed through between the anvil roll 200 and the ultrasonic horn 330 to undergo output of the ultrasonic vibration on the predetermined region 60.

(3) Working of Ultrasonic Bonding Device

Figure 6:
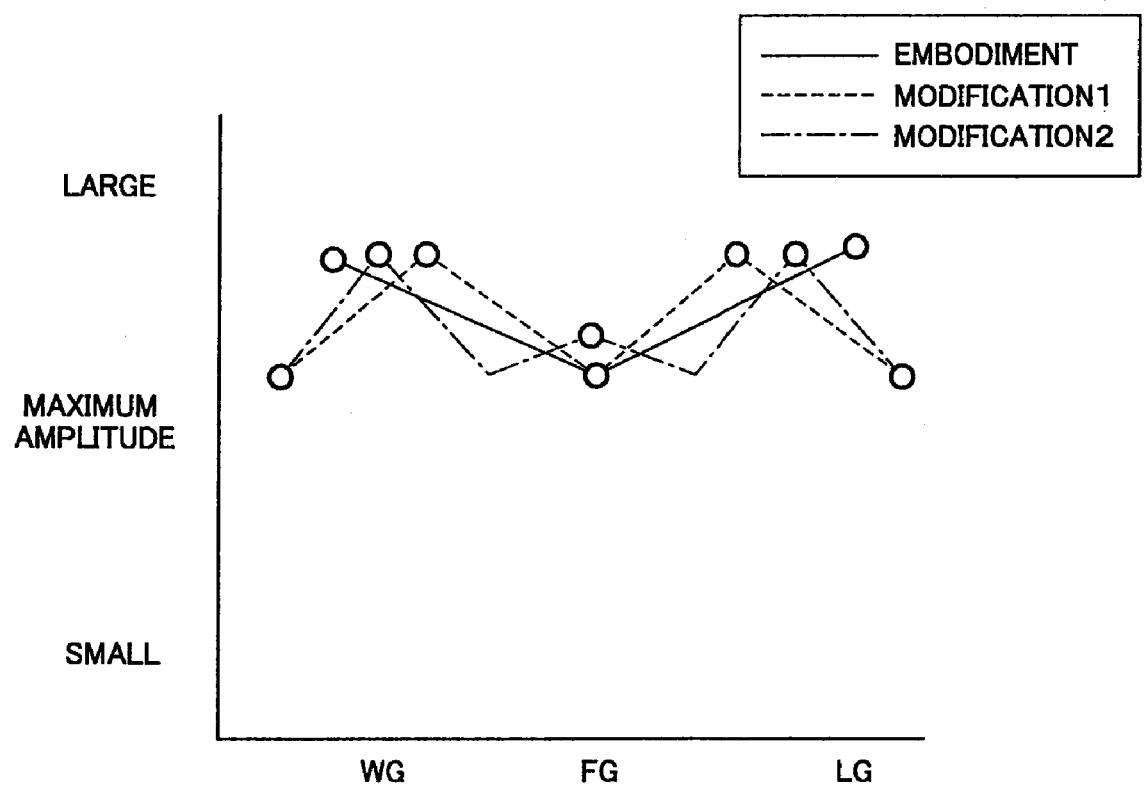
FIG. 6 is a graph showing an image of a maximum amplitude according to this embodiment.

Next, a working of the ultrasonic bonding device 100 according to this embodiment will be described with reference to FIG. 6. FIG. 6 is a graph showing an image of a maximum amplitude according to this embodiment.

In the ultrasonic bonding device 100, the anvil roll 200, i.e., the projecting part 220, rotates in association with the conveyance of the first web 10A and the second web 20A. At this time, the projecting part 220 and the ultrasonic horn 330 work with each other to pinch the first web 10A and the second web 20A. Thereby, the ultrasonic vibration generated by the ultrasonic vibrator 310 is outputted to the predetermined region 60 of the first web 10A and the second web 20A from the ultrasonic horn 330.

At this time, as shown by the solid line in FIG. 6, a central maximum amplitude of the ultrasonic vibration outputted from the central output portion 332A to the center region 60C is smaller than an end maximum amplitude of the ultrasonic vibration outputted from each of the both-ends output portions 332B to a corresponding one of the both-ends regions 60S due to the above-described shape of the ultrasonic horn 330. For this reason, a central bonding strength of the center region 60C bonded by the central output portion 332A is smaller than an end bonding strength of each of the both-ends regions 60S bonded by a corresponding one of the both-ends output portions 332B.

Here, ultrasonic vibration is converted from electrical energy by the ultrasonic vibrator 310. The ultrasonic vibration thus converted turns into longitudinal vibration in the diameter direction of the anvil roll 200 by the ultrasonic horn 330, after the amplitude thereof is amplified via the booster 320. The output surface 332 at the side of the anvil roll 200 of the ultrasonic horn 330 works with the projecting parts 220 to pinch the first web 10A and the second web 20A, so that the ultrasonic vibration is applied to the predetermined region 60.

(4) Manufacturing Method of Absorbent Article

Figure 7:
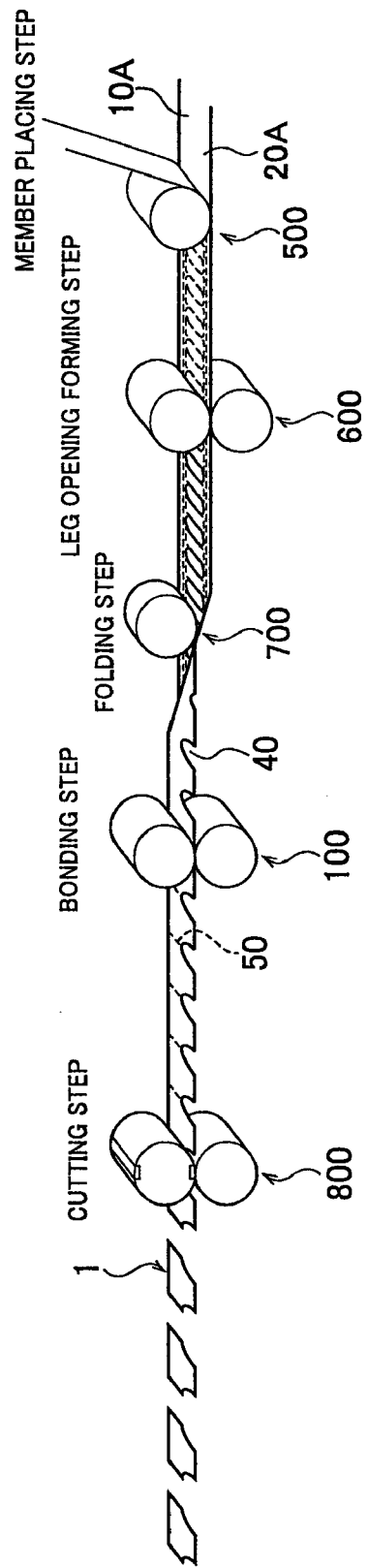
FIG. 7 is a schematic view showing a manufacturing method of the absorbent article 1 according to this embodiment.

Next, a manufacturing method of the absorbent article 1 according to this embodiment will be described with reference to the drawings. FIG. 7 is a schematic view showing the manufacturing method of the absorbent article 1 according to this embodiment.

As shown in FIG. 7, the manufacturing method of the absorbent article 1 includes at least a member placing step, a leg opening forming step, a folding step, a bonding step, and a cutting step. Here, a continuous body including the first web 10A which constitutes the front waistband part 10 and the second web 20A which constitutes the rear waistband part 20 is conveyed by an conveying machine not shown (for example, a belt conveyor device) between each step.

(4-1) Member Placing Step

At the member placing step, various members are placed on the continuous body including the first web 10A and the second web 20A (for example, a continuous body of an outer sheet) by a member mounting device 500. The various members include gathers (the waist gather 2 and the leg gather 3), a tarpaulin, an absorber, a top sheet (not shown), for example.

(4-2) Leg Opening Forming Step

AT the leg opening forming step, a cut roll 600 forms the leg openings 40 (i.e., leg holes) in the continuous body on which the various members are placed after the member placing step.

(4-3) Folding Step

At the folding step, a folding device 700 folds into two the continuous body in which the leg openings 40 are formed after the leg opening forming step. In other words, the first web 10A and the second web 20A are overlapped with each other at the folding step.

(4-4) Bonding Step

At the bonding step, after the folding step, the ultrasonic vibration generated by the ultrasonic vibrator 310 which constitutes the above-described ultrasonic bonding device 100 is outputted to the predetermined region 60 of the first web 10A and the second web 20A from the output surface 332 of the ultrasonic horn 330, so that the predetermined region 60 is bonded.

Here, the first web 10A and the second web 20A are conveyed in an overlapped state between the anvil roll 200 and the ultrasonic horn 330 by the above-described conveying machine.

(4-5) Cutting Step

At the cutting step, after the bonding step, a cutting device 800 cuts a portion between the first predetermined region 61 and the second predetermined region 62 in the cross direction CD, so that the absorbent article 1 is formed.

(5) Operation and Effect

According to the embodiment, the central maximum amplitude of the ultrasonic vibration is smaller than the end maximum amplitude thereof. For this reason, the central bonding strength is smaller than the end bonding strength. Therefore, when a wearer puts on and off the absorbent article 1 (at the time of putting on and off), the waist portion 50W and the leg portion 50L become difficult to be separated, thereby improving durability of the absorbent article 1. Further, since the waist portion 50W is not separated easily, when the wearer puts on the absorbent article 1 (at the time of putting on), the absorbent article 1 easily fits the waist portion of the wearer. Meanwhile, since the leg portion 50L is not separated easily, the leg portion 50L does not be loosened, thereby preventing excrement from the wearer from leaking from the leg portion 50L (a so-called leakage prevention capability is deteriorated).

Further, since the bonding strength of the whole predetermined region 60 does not become strong, when the wearer disposes of the absorbent article 1 (at the time of disposal), it becomes easy to tear the bonded part 50 (a so-called disassembling property improves). At the time of the usual disposal, a portion from the waist portion 50W to the leg portion 50L can be unstuck finely without the first web 10A and the second web 20A being torn in a waistband direction, by separating the bonded part from the waist portion 50W.

As describe above, the waist portion 50W and the leg portion 50L of the absorbent article 1 can be made less likely to be separated, while keeping basic properties originally needed, such as the durability of the absorbent article 1 at the time of putting on and off and the improvement of the leakage prevention capability at the time of putting on, and additional properties, such as the disassembling property at the time of disposal.

(6) Modifications

The ultrasonic bonding device 100 according to the above-described embodiment may be changed as follows. Note that, the same reference numerals are given to the same portion as the ultrasonic bonding device 100 according to the above-described embodiment, and different portions will be mainly described.

The ultrasonic bonding device 100 according to the above-described embodiment includes one ultrasonic horn 330. On the other hand, an ultrasonic bonding device 101 according to a modification includes multiple ultrasonic horns 330. The ultrasonic horn 330 which constitutes the ultrasonic bonding device 101 according to the modification does not have special shape but has a general shape, as in the above-described embodiment.

Specifically, as shown in FIG. 8, an output surface 332 in the ultrasonic horn 330 according to the modification includes therein a center portion 332C located at the center of three portions into which the output surface 332 is equally divided, and both-ends portions 332D located at both sides of the center portion 332C in the cross direction CD.

The ultrasonic horn 330 according to the modification is connected to an ultrasonic vibrator 310 in an input center region including the center of an input surface 331 corresponding to an output center region which includes the center of the output surface 332. Therefore, a maximum amplitude of the ultrasonic vibration outputted from the center portion 332C is larger than the maximum amplitude of the ultrasonic vibration outputted from the both-ends portions 332D.

(6-1) First Modification

First, a configuration of an ultrasonic bonding device 101A according to a first modification will be described with reference to the drawings. FIG. 9 is a view showing the ultrasonic bonding device 101A according to the first modification.

As shown in FIG. 9, the ultrasonic bonding device 101A is provided with two ultrasonic horns 330. In other words, the two ultrasonic horns 330 are independently provided. Ultrasonic vibrators 310 (not shown in FIG. 9, see FIG. 3) described in the embodiment are respectively provided to the two independent ultrasonic horns 330.

The two ultrasonic horns 330 are arranged so as to be aligned in the cross direction CD. An attaching position of each of the two ultrasonic horns 330 can be adjusted individually. In other words, it is possible to adjust clearances, variations, a relative position or the like of the two ultrasonic horns 330 with projecting parts 220 of an anvil roll 200. For example, the two ultrasonic horns 330 are movable in the cross direction CD, the conveyance direction MD, the diameter direction of the anvil roll 200, and the like.

Two ultrasonic vibrators 310 provided on the two ultrasonic horns 330 generate the same ultrasonic vibration respectively. For this reason, the maximum amplitude of the ultrasonic vibration outputted from a center portion 332C is larger than the maximum amplitude of the ultrasonic vibration outputted from both-ends portions 332D (see the dashed line of FIG. 6).

Two output surfaces 332 which constitute the two ultrasonic horns 330 aligned in the cross direction CD are provided with a central output portion 332A, and both-ends output portions 332B. In other words, the central output portion 332A and the both-ends output portions 332B are formed of the output surfaces 332 which constitute the two ultrasonic horns 330 aligned in the cross direction CD.

In other words, the central output portion 332A is formed of one end portion 332D of one ultrasonic horn 330 and one end portion 332D of the other ultrasonic horn 330. The both-ends output portions 332B are formed of portions other than the end portions 332D which constitute the central output portion 332A.

Thus, since the two ultrasonic horns 330 are arranged so as to be aligned in the cross direction CD, the central maximum amplitude of the ultrasonic vibration outputted from the central output portion 332A to a center region 60C is smaller than the end maximum amplitude of the ultrasonic vibration outputted from each of the both-ends output portions 332B to a corresponding one of both-ends regions 60S. For this reason, the central bonding strength of the center region 60C bonded by the central output portion 332A becomes smaller than the end bonding strength of each of the both-ends regions bonded by a corresponding one of the both-ends output portions 332B.

According to the ultrasonic bonding device 101A according to the first modification, the waist portion 50W and the leg portion 50L of the absorbent article 1 can be made difficult to be separated, while keeping the basic properties and the additional properties, as is the case with the operation and effect of the above-described embodiment. Further, since the ultrasonic horn 330 according to the first modification does not need to be a special shape, a general-purpose article can be used for the ultrasonic horn 330.

According to the ultrasonic bonding device 101A according to the first modification, since an attaching position of each of the two ultrasonic horns 330 can be adjusted individually, it is possible to adjust the output of the ultrasonic vibration from the central output portion 332A and the output of the ultrasonic vibration from the both-ends output portions 332B.

For example, changing an interval between the two ultrasonic horns 330 aligned in the cross direction CD, and the projecting parts 220 of the anvil roll 200 (i.e., a clearance in the central output portion 332A) makes it possible to adjust a relation between a pressure of the ultrasonic vibration in the central output portion 332A and a pressure of the ultrasonic vibration in the both-ends output portions 332B. Further, changing a relative position of the two ultrasonic horns 330 makes it possible to adjust a relation between the central maximum amplitude and the end maximum amplitude.

(6-2) Second Modification

First, a configuration of an ultrasonic bonding device 101B according to a second modification will be described with reference to the drawings. FIG. 10 is a view showing the ultrasonic bonding device 101B according to the second modification.

As shown in FIG. 10, the ultrasonic bonding device 101B is provided with three ultrasonic horns 330. In other words, the three ultrasonic horns 330 are independently provided. Ultrasonic vibrators 310 (not shown in FIG. 10, see FIG. 3) described in the embodiment are respectively provided to the three independent ultrasonic horns 330. The three ultrasonic horns 330 are arranged so as to be aligned in the cross direction CD. An attaching position of each of the three ultrasonic horns 330 can be adjusted individually. In other words, it is possible to adjust clearances, variations, a relative position or the like of the three ultrasonic horns 330 with projecting parts 220 of an anvil roll 200. For example, three ultrasonic horns 330 are movable in the cross direction CD, the conveyance direction MD, the diameter direction of the anvil roll 200, and the like.

The ultrasonic vibration generated by the ultrasonic vibrator 310 located at the center of the three ultrasonic vibrators 310 provided on the three ultrasonic horns 330 is smaller than the ultrasonic vibration generated by other ultrasonic vibrators 310 (see the dashed-dotted line of FIG. 6).

Three output surfaces 332 which constitute the three ultrasonic horns 330 aligned in the cross direction CD are provided with a central output portion 332A, and both-ends output portions 332B. In other words, the central output portion 332A and the both-ends output portions 332B are formed of the output surfaces 332 which constitute the three ultrasonic horns 330 aligned in the cross direction CD.

In other words, the central output portion 332A is formed of the output surface 332 of the ultrasonic horn 330' located at the center of the three ultrasonic horns 330. The both-ends output portions 332B are formed of the output surfaces 332 in the two ultrasonic horns 330" located at both sides of the ultrasonic horn 330' in the cross direction CD.

Thus, the central maximum amplitude of the ultrasonic vibration outputted from the central output portion 332A to a center region 60C can be made smaller than the end maximum amplitude of the ultrasonic vibration outputted from each of the both-ends output portions 332B to a corresponding one of the both-ends regions. For this reason, the central bonding strength of the center region 60C bonded by the central output portion 332A becomes smaller than the end bonding strength of each of the both-ends regions bonded by a corresponding one of the both-ends output portions 332B.

Figure 11:
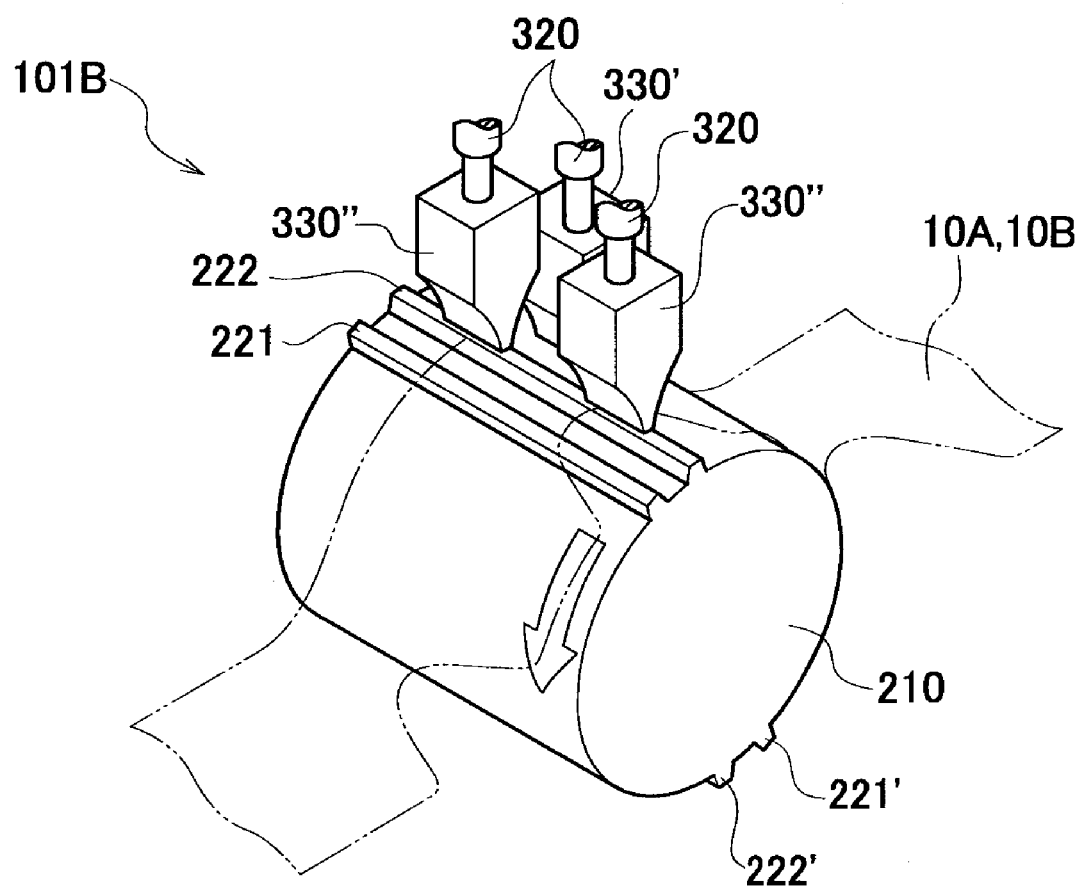
FIG. 11 is a view showing the ultrasonic bonding device 101B according to the second modification (No. 2).

Although the description has been made here that the three ultrasonic horns 330 are arranged so as to be aligned in the cross direction CD in the ultrasonic bonding device 101B according to the second modification, not limited to this, as shown in FIG. 11, the ultrasonic horn 330' may shift in the conveyance direction MD (i.e., a rotational direction of the anvil roll 200) than the other two ultrasonic horns 330".

According to the ultrasonic bonding device 101B according to the second modification, the waist portion 50W and the leg portion 50L of the absorbent article 1 can be made difficult to be separated, while keeping the basic properties and the additional properties, as is the case with the operation and effect of the above-described embodiment. Further, since the ultrasonic horn 330 according to the second modification does not need to be a special shape as is the case with the first modification, a general-purpose article can be used for the ultrasonic horn 330.

According to the ultrasonic bonding device 101B according to the second modification, since an attaching position of each of the three ultrasonic horns 330 can be adjusted individually, it is possible to adjust the output of the ultrasonic vibration from the central output portion 332A and the output of the ultrasonic vibration from the both-ends output portions 332B.

For example, changing an interval between the three ultrasonic horns 330 aligned in the cross direction CD, and the projecting parts 220 of the anvil roll 200 (i.e., a clearance in the central output portion 332A) makes it possible to adjust a relation between a pressure of the ultrasonic vibration in the central output portion 332A and a pressure of the ultrasonic vibration in the both-ends output portions 332B. Further, changing a relative position of the three ultrasonic horns 330 makes it possible to adjust a relation between the central maximum amplitude and the end maximum amplitude.

(7) Other Embodiments

As described above, the contents of the present invention has been disclosed through the embodiments of the present invention. However, it should not be understood that the statement and the drawings which make a part of this disclosure limit the present invention. Various alternative embodiments, examples, and operational techniques will be apparent to those skilled in the art from this disclosure.

For example, the embodiments of the present invention can be changed as follows. Specifically, the ultrasonic bonding device is described as an example, and is not necessarily limited to the device described in the embodiments. It is needless to say that a device may be used which can apply ultrasonic vibration to the predetermined region 60 of the first web 10A and the second web 20A in a region corresponding to the bonded part 50 of the absorbent article 1.

Further, there is no restriction in particular about a shape, a structure, an arrangement, and the like of the ultrasonic horn 330, and similarly, there is no restriction in particular about a shape, a structure, an arrangement, and the like of the anvil roll 200 (the projecting part 220), and they can be chosen suitably depending on the purpose.

Thus, the present invention naturally includes various embodiments and the like which have not been described here. Therefore, the technical scope of the present invention is defined only by the invention specific matter according to the appended claims which are appropriate from the above-described description.

What is claimed is:

1. A manufacturing method of an absorbent article including a first web which constitutes a front waistband part, and a second web which constitutes a rear waistband part, the method comprising:

a step A of conveying the first web and the second web in an overlapped state between an anvil part and a vibrator which are provided to an ultrasonic bonding device; and a step B of bonding predetermined regions provided to the first web and the second web with a predetermined interval in a conveyance direction of the first web and the second web by outputting an ultrasonic vibration from an output part of the vibrator to the predetermined regions, the ultrasonic vibration generated by an oscillator provided to the ultrasonic bonding device, wherein the output part includes:
  a central output portion configured to output the ultrasonic vibration to a center region of three equal regions into which each predetermined region is divided in a cross direction crossing the conveyance direction; and
  both-ends output portions configured to output the ultrasonic vibration respectively to both-ends regions of the three equal regions into which each predetermined region is divided, the both-ends regions located at both sides in the cross direction of the center region,
a central maximum amplitude of the ultrasonic vibration outputted from the central output portion to the center region is smaller than an end maximum amplitude of the ultrasonic vibration outputted from each of the both-ends output portions to a corresponding one of the both-ends regions, and
a central bonding strength of the center region bonded by the central output portion is smaller than an end bonding strength of each of the both-ends regions bonded by a corresponding one of the both-ends output portions.

2. The manufacturing method of an absorbent article according to claim 1, wherein
  a plurality of the vibrators are independently provided, and
  the oscillator is provided in each of the independent vibrators.

3. The manufacturing method of an absorbent article according to claim 2, wherein the independent vibrators are arranged so as to be aligned in the cross direction.

4. The manufacturing method of an absorbent article according to any one of claims 1 to 3, wherein
  a plurality of the anvil parts are independently provided, and
  the independent anvil parts are arranged so as to be aligned in the conveyance direction.

5. The manufacturing method of an absorbent article according to claim 1, wherein the central maximum amplitude is made smaller than the end maximum amplitude, and the central bonding strength is made smaller than the end bonding strength, by changing a shape of the vibrator.

6. The manufacturing method of an absorbent article according to claim 1, further comprising a step C of overlapping the first web and the second web before the step A.

7. The manufacturing method of an absorbent article according to claim 1, wherein
  each predetermined region includes:
    a first predetermined region; and
    a second predetermined region which is adjacent to the first predetermined region with an interval smaller than the predetermined interval in the conveyance direction, and
  further comprising a step D of cutting a line between the first predetermined region and the second predetermined region in the cross direction after the step B in order to form the absorbent article.

* * * * *